United States Patent [19]

Lehman et al.

[11] Patent Number: 5,047,399
[45] Date of Patent: Sep. 10, 1991

[54] HYDROPHOBIC PSEUDO-PEPTIDES

[75] Inventors: Laura S. Lehman, New YOrk, N.Y.; Michael F. Czarniecki, Westfield, N.J.

[73] Assignee: Schering Corporation, Kenilworth, N.J.

[21] Appl. No.: 218,402

[22] Filed: Jul. 13, 1988

[51] Int. Cl.[5] .................... A61K 37/02; C07K 7/06
[52] U.S. Cl. .................................. 514/17; 514/16; 514/18
[58] Field of Search ............................. 514/16, 17, 18

[56] References Cited

U.S. PATENT DOCUMENTS

| | | | |
|---|---|---|---|
| 4,609,641 | 9/1986 | Evan et al. | 514/18 |
| 4,629,724 | 12/1986 | Ryono et al. | 514/18 |
| 4,645,759 | 2/1987 | Luly et al. | 530/331 |
| 4,725,584 | 2/1988 | Luly et al. | 530/331 |
| 4,766,109 | 8/1988 | Czarniecki et al. | 530/330 |

OTHER PUBLICATIONS

Gaeta et al., "Small Peptide Inhibitors of Smooth Muscle Myosin Light Chain Kinase", Journal of Medicinal Chemistry, 33, 964, 1990.

Primary Examiner—Lester L. Lee
Assistant Examiner—S. G. Marshall
Attorney, Agent, or Firm—Anita W. Magatti; James R. Nelson

[57] ABSTRACT

Novel hydrophobic psuedo-peptides of formula I

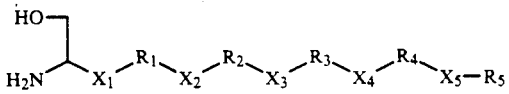

wherein $R_1$ is lower alkyl or $-CH_2 CONR_6R_7$;

$R_2$, $R_3$, $R_4$ and $R_5$ are independently lower alkyl, cycloalkyl lower alkyl, aryl lower alkyl, heteroaryl lower alkyl, aryl lower alkoxy, substituted aryl lower alkyl, wherein the aryl portion is substituted with 1-3 substituents independently selected from lowr alkyl, hydroxyl, lower alkoxy and halogeno, substituted heteroaryl lower alkyl wherein the substituents on the heteroaryl portion are as defined for aryl lower alkyl, substituted cycloalkyl lower alkyl, wherein the substituents on the cycloalkyl portion are as defined for aryl lower alkyl, and substituted aryl lower alkoxy wherein the substituents are as defined for aryl lower alkyl;

$R_6$ and $R_7$ are independently hydrogen or lower alkyl;

$X_1$, $X_2$, $X_3$, $X_4$ and $X_5$ are independently

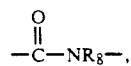

cis or trans $-CR_8=CR_9-$, $-CHR_8CHR_9-$, $-CH_2NR_8-$,

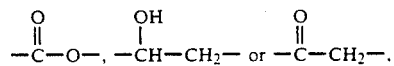

provided that when $R^4$ is methyl, $X_4$ is not $-CONH-$;
$R_8$ and $R_9$ are independently hydrogen or lower alkyl;
the pharmaceutically acceptable salts thereof,a nd pharmaceutical compositions thereof, useful in the treatment of hypertension are disclosed.

15 Claims, No Drawings

HYDROPHOBIC PSEUDO-PEPTIDES

SUMMARY OF THE INVENTION

The present invention relates to hydrophobic pseudo-peptides which have antihypertensive activity.

The invention also relates to pharmaceutical compositions comprising the hydrophobic pseudo-peptides of this invention, and to a method of treating hypertension comprising administering a hydrophobic pseudo-peptide of this invention to a hypertensive

DESCRIPTION OF THE INVENTION

The hydrophobic pseudo-peptides of this invention are represented by the following formula:

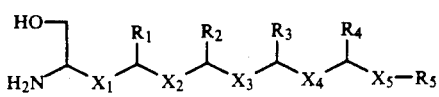

wherein $R_1$ is lower alkyl or —$CH_2CONR_6R_7$; $R_2$, $R_3$, $R_4$ and $R_5$ are independently lower alkyl, cycloalkyl lower alkyl, aryl lower alkyl, heteroaryl lower alkyl, aryl lower alkoxy, substituted aryl lower alkyl, wherein the aryl portion is substituted with 1-3 substituents independently selected from lower alkyl, hydroxy, lower alkoxy and halogeno, substituted heteroaryl lower alkyl wherein the substituents on the heteroaryl portion are as defined for aryl lower alkyl, substituted cycloalkyl lower alkyl, wherein the substituents on the cycloalkyl portion are as defined for aryl lower alkyl, and substituted aryl lower alkoxy wherein the substituents are as defined for aryl lower alkyl;

$R_6$ and $R_7$ are independently hydrogen or lower alkyl;

$X_1, X_2, X_3, X_4$ and $X_5$ are independently

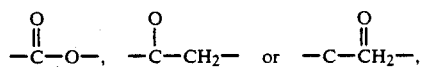

cis or trans —$CR_8=CR_9$—, —$CHR_8CHR_9$—, —$CH_2NR_8$—, $$-\overset{O}{\underset{\|}{C}}-O-,\quad -\overset{O}{\underset{|}{C}}-CH_2-\quad \text{or}\quad -\overset{O}{\underset{\|}{C}}-CH_2-,$$

provided that when $R_4$ is methyl, $X_4$ is not —CONH—;

$R_8$ and $R_9$ are independently hydrogen or lower alkyl;

and the pharmaceutically acceptable salts thereof.

Compounds of the present invention are related to the hydrophobic peptides disclosed in U.S. Ser. No. 919,950, filed Oct. 17, 1986, now U.S. Pat. No. 4,766,109 but the present compounds incorporate peptide bond isosteres which impart greater resistance to esterase and peptidase enzymes, and therefore exhibit greater stability than peptides.

As used herein the term "lower alkyl" refers to straight or branched chain alkyl groups of 1 to 6 carbon atoms, and lower alkoxy similarly refers to alkoxy groups having 1 to 6 carbon atoms. "Cycloalkyl" means cyclic alkyl groups of 3-7 carbon atoms.

As used herein the term "aryl" means phenyl; a polycyclic phenyl fused ring system having 10-14 carbon atoms; or a polycyclic phenyl ring system wherein two or more phenyl rings are bonded to each other by ring carbons or two or more phenyl rings are bonded to an alkyl group. Examplse of aryl groups ar ephenyl, naphthyl, anthracenyl, phenanthrenyl, fluorenyl, biphenyl and diphenylmethyl. All positional isomers are contemplated, e.g. 1-naphthyl and 2-naphthyl.

"Heteroaryl" means a monocylcic or bicyclic fused ring system comprising 5-10 atoms wherein 1 or more ring atoms are independently selected from nitrogen, oxygen or sulfur and the remaining ring atoms are carbon. Examples of heteraryl groups are pyrrolyl, furyl, pyrazolyl, thiophenyl, pyranyl, pyridyl, pyrimidyl, pyrizinyl, thiopyranyl and their benzo fused analogs.

"Halogeno" means chloro, fuloro, bromo or iodo.

Preferred compounds of formula I are those wherein $R_1$ is methyl or —$CH_2CONH_2$. Also preferred are compounds of formula I wherein $R_2$ is 2-propyl. Preferred are compounds of formula I wherein each of $R_3$, $R_4$ and $R_5$ is indepndnetly aryl lower alkyl or substituted aryl lower alkyl. A more preferred definition for each of $R_3$ and $R_5$ includes benzyl, 4-hydroxybenzyl and 4-methoxybenzyl. Another group of more preferred compounds are those wherein $R_4$ is phenylpropyl, 4-hydroxyphenylpropyl or 4-methoxyphenylpropyl. A preferred definition for each of $X_1, X_2$ and $X_3$ is —CONH—, a preferred definition for $X_4$ is trans vinylene, and a preferred definition for $X_5$ is ethylene.

More preferred are compounds of formula I wherein $R_1$ is —$CH_2CONH_2$, $R_2$ is 2-propyl, $X_1, X_2$ and $X_3$ are each —CONH—, $X_4$ is trans vinylene and $X_5$ is ethylene.

A more preferred compound of formula I therefore has the following formula Ia:

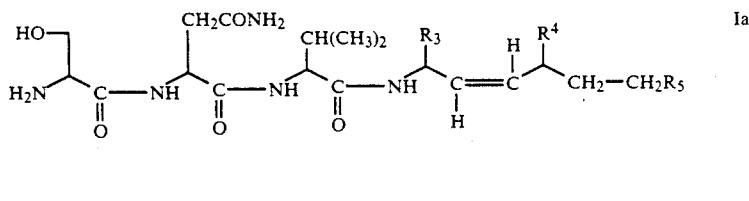

wherein $R_3, R_4$ and $R_5$ are as defined above.

Compounds of this invention form salts with various inorganic and organic acids and bases. Such salts include salts prepared with organic and inorganic acids, e.g. HCl, HBr, $H_2SO_4$, $H_3PO_4$, methanesulfonic acid, toluenesulfonic acid, maleic acid, furmaric acid and camphorsulfonic acid. Salts prepared with bases include ammonium salts, alkali metal salts, e.g. sodium and potassium salts, and alkaline earth salts, e.g. calcium and magnesium salts. Hydrochloride salts are preferred.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of the instant invention include various stereoisomers as indicated in the following structural formula wherein chiral centers are marked with an asterisk and numbered:

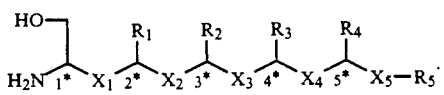

and wherein $R_1$–$R_5$ and $X_1$–$X_5$ are as defined above. Chiral centers may also be present in side chains at $R_2$–$R_5$, depending on the group present. Preferred stereochemistry at centers 2 and 3 is "S", while centers 4 and 5 may be "R" or "S".

Compounds of the present invention can be prepared using methods well known in the art. Typically, compounds of the invention are prepared by successively adding on the desired —XCHR— fragments. When an "X" group of a compound of formula I is a conventional peptide bond, i.e. —CONH— or —CONR$^8$, methods well known in peptide synthesis can be used to form the group. Typically, an α-N-carbamoyl protected amino acid and a carboxyl-protected amino acid are reacted at room temperature in an inert solvent such as dimethylformamide in the presence of coupling agents such as dicyclohexyl carbodiimide (DCC) and 1-hydroxybenzotriazole in the presence of a base such as N-methylmorpholine. Suitable N-protecting groups are well known in the art, with t-butyloxycarbonyl herein preferred.

Similarly, when X is a carboxylic ester, i.e.,

an α-N-carbamoyl protected amino acid and an OH-containing compound are reacted in the presence of coupling agents such as 1-(3-dimethylaminopropyl)-3-ethyl carbodiimide and 4-dimethylaminopyridine.

Alkenes, wherein X is —CR$_8$=CR$_9$—, can be prepared using the Wittig olefin synthesis or known modifications thereof. Catalytic reduction (e.g. hydrogenation) of the alkene can be performed to prepare compounds wherein X is —CHR$_8$CHR$_9$—.

Compounds wherein X is an iminomethylene group (i.e. —CH$_2$NR$_8$—) can be prepared by borane reduction of the desired amide bond or by reductive amination with sodium cyanoborohydride of the imine formed by appropriately protected amino aldehyde and amino acid components.

For compounds wherein X is hydroxyethylene, a Grignard-type reaction with an amino-protected aldehyde and a magnesium bromide compound can be carried out. The hydroxy compounds can be oxidized using a reagent such as pyridinium dichromate to obtain the ketomethylene compounds (i.e. wherein X is

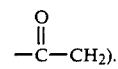

When preparing compounds of this invention comprising a hydroxyphenyl substituent, it is necessary to employ suitable hydroxy-protecting groups, e.g. t-butyl or methyl ethers. Removal of methyl ethers requires an additional deprotection step, e.g. treatment with boron tribromide in methylene chloride.

Following is a general reaction scheme for preferred compounds of the present invention:

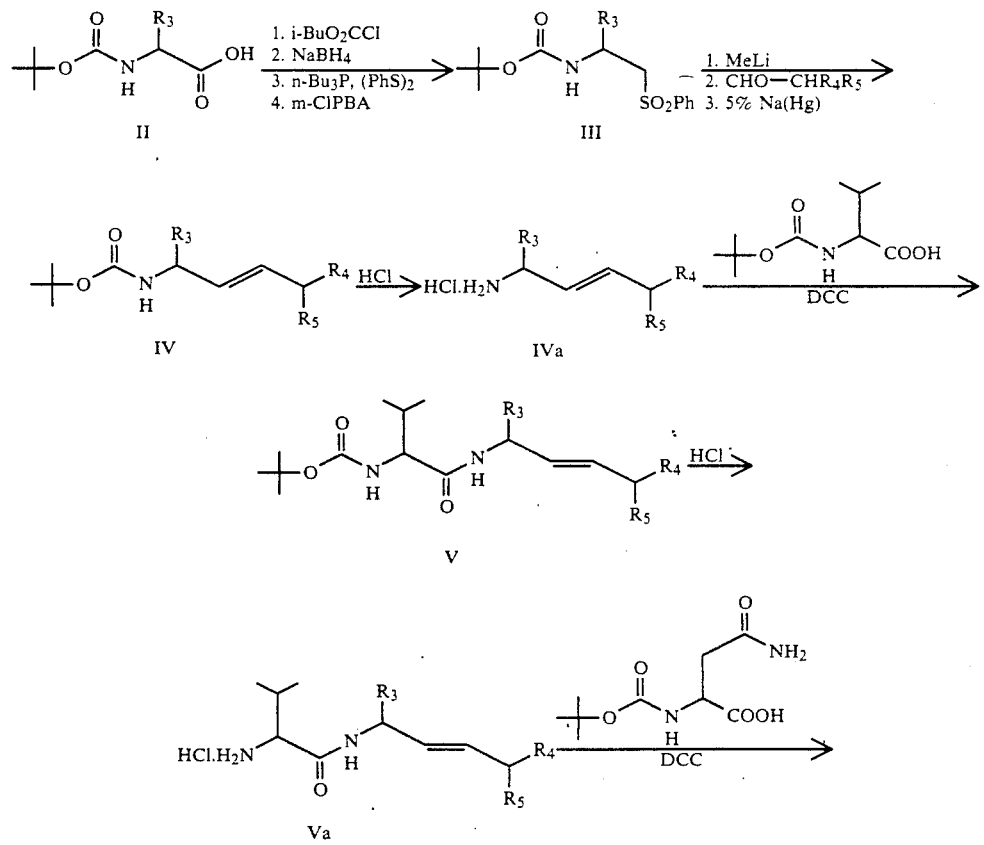

-continued

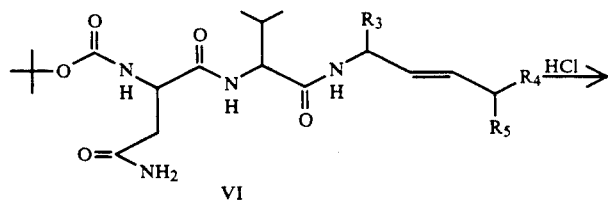
VI

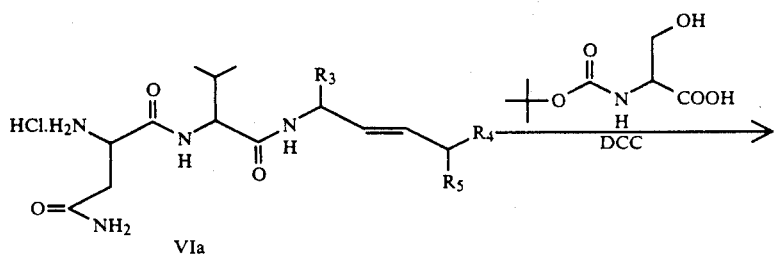
VIa

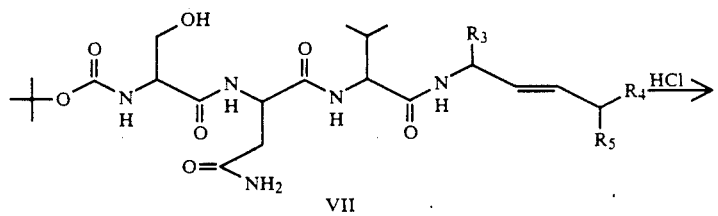
VII

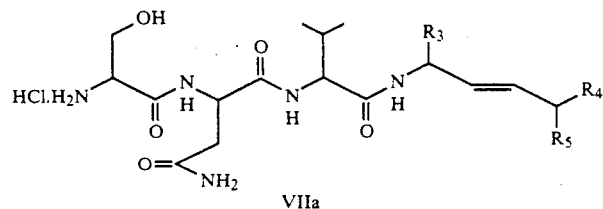
VIIa

The starting hydrophobic amino acids of formula II are also prepared by well-known methods. For example, a malonic ester-type synthesis reacting $R^3$-halides (preferably $R^3$-Br) with diethyl acetamidomalonate followed by hydrolysis may be used to prepare the $R^3$-containing amino acid, which may then be N-protyected by conventional means. Starting compounds of formula X ($R^3$-Br) are readily available by known methods. A schematic example of such syntheses follows:

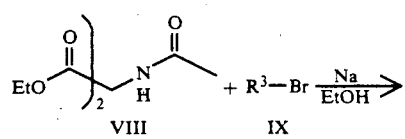
VIII    IX

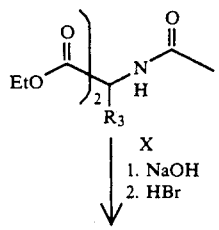
X
1. NaOH
2. HBr

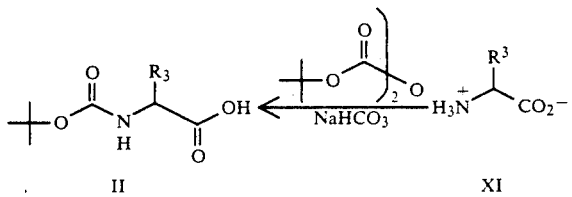
II    XI

Following is an example of the preparation of compounds of the present invention.

EXAMPLE 1

(S)-SERYL-(S)-ASPARAGINYL-N-[7-PHENYL-1-(PHENYLMETHYL)4-(3-PHENYLPROPYL)-2-HEPTENYL-(S)-VALINAMIDE A.

(1,1-Dimethylethyl)-2-phenyl-1-[(phenylsulfonyl)methyl]ethyl carbamate

Dissolve N-(tert-butyloxycarbonyl)-(S)phenylalanine (26 g) in tetrahydrofuran (THF) (200 ml), cool to 0° and treat with N-methylmorpholine (10 g) followed by isobutylchloroformate (13 g) dropwise. Stir 0 minutes, add sodium borohydride (3.8 g), and stir 1 hour at room temperature. Neutralize the solution with saturated aqueous ammonium chloride ($Na_4Cl$), add ethyl acetate (EtOAc), and wash the organic layer successively with saturated aqueous sodium bicarbonate ($NaHCO_3$), 10% citric acid, and saturated aqueous sodium chloride. Dry the organic layer over sodium sulfate ($Na_2SO_4$), filter, and evaporate solvent. Combine 12.6 g of the residue with diphenyldisulfide (18 g) and tri-n-butylphosphine (21 g) in THF (150 ml). Stir 12 hours and evaporate the solvent. uspend the residue in diethylether ($Et_2O$) and wash with 1N sodium hydroxide (NaOH). Dry the organic layer over $Na_2SO_4$, filter, and evaporate the solvent. Dissolve the residue in methylene chloride ($CH_2Cl_2$) (400 ml), cool to 0° C., and add meta-chloroperbenzoic acid (50 g) in small portions over 30 minutes. Stir 10 hours and filter the precipitate. Cool the filtrate to 0° C. and treat with 10% aqueous sodium sulfite ($Na_2SO_3$) (375 ml). Wash the organic layer successively with saturated aqueous $NaHCO_3$ and sodium chloride. Dry the organic layer over $Na_2SO_4$, filter, and evaporate the solvent to give the title compound. $R_f$ (silica gel; $CH_2Cl_2$: $CH_3OH$, 98:2)=0.59

B. (1,1-Dimethylethyl)-7-phenyl-1-(phenylmethyl)-4-(3-phenylpropyl)-2-heptenylcarbamate Suspend the product prepared in Part A (0.94 g) in THF (10 ml), cool to −78° C. and add 1.4M methyl lithium in $EtO_2$ (3.6 ml). Warm the solution to 0° C., stir 30 minutes, and cool to −78° C. Add 5-phenyl-2-(phenylpropyl)-1-pentanal (0.7 g) stir 1 hour, quench with saturated aqueous $NH_4Cl$ (10 ml) and allow the reaction to warm to room temperature. Extract the reaction mixture with $Et_2O$, dry the organic layer with $Na_2SO_4$, filter, and evaporate the solvent. Dissolve the residue in methanol ($CH_3OH$) (8 ml), cool to 0° C., and add disodium hydrogen phophate ($Na_2HPO_4$) (0.4 g) and 5% sodium amalgam (5 g). Stir 4 hours and partition the reaction mixture between water and $CH_2Cl_2$ Dry the organic layer over $Na_2SO_4$, filter, and evaporate the solvent to give the title compound. $R_f$ (silica gel; Hexane:Et20, 75:25)=0.55.

C. (1,1-Dimethylethyl)−2-methyl−1-[[[7-phenyl-1-(phenylmethyl)-4-(3-phenylpropyl)-2-heptenyl]amino]-carbonyl]propylcarbamate Add 6M HCl in dioxane (10 ml) to the product of Part B (0.5 g). Stir 10 minutes and evaporate excess acid and solvent. Add to this residue N-α-tert-butyloxy-carbonyl-(S)-valine (0.22 g), 1-(3-dimethyllaminopropyl)-3-ethylcarbodiimide (DEC) (0.19 g), 1-hydroxybenzotriazole hydrate (HOBT) (0.15 g), N-methylmorpholine (0.1g), and 2 ml anhydrous dimethylformamide (DMF). Stir 12 hours and evaporate the solvent. Suspend the residue in EtOAc and wash successively with saturated aqueous $NaHCO_3$, 10% citric acid, and water. Dry the organic layer over $Na_2SO_4$, filter, and evaporate the solvent to obtain the title compound. $R_f$ (silica gel; $CH_2Cl_2$:$CH_3OH$, 95:5)=0.58.

D. $N^2$-[(1,1-dimethylethoxy)carbonyl]-(S)-asparaginyl-N-[7-phenyl−1-(phenylmethyl)-4-(3-phenyl-propyl)-2-heptenyl-(S)-valinamide Add 6M HCl in dioxane (10 ml) to the product of Part C (0.6 g). Stir 10 minutes and evaporate excess acid and solvent. Add to this residue N-α-tert-butyloxycarbonyl-(S)-asparagine (0.23 g), DEC (0.19 g), HOBT (0.15 g), N-methylmorpholine (0.1 g), and anhydrous DMF (2 ml). Stir 12 hours and evaporate the solvent. Suspend the residue in EtOAc and wash successively with saturated aqueous $NaHCO_3$, 10% citric acid, and water. Dry the organic layer over $Na_2SO_4$, filter, and evaporate the solvent to obtain the title compound. $R_f$ (silica gel; $CH_2Cl_2$:$CH_3OH$, 95:5)=0.34.

E. (S)-Seryl-(S)-aspraginyl-N-[7-phenyl-1-(phenylmethyl)-4-(3-phenylpropyl)-2-heptenyl]-(S)-valinamide Add 6M HCl in dioxane (10 ml) to the product of Part D (0.75 g). Stir 10 minutes and evaporate the excess acid and solvent. Add to this residue N-α-tert-butyloxycarbonyl-(S)-serine (0.2 g), DEC (0.19 g), HOBT (0.15 g), N-methylmorpholine (0.1 g), and anhydrous DMF (2 ml). Stir 12 hours and evaporate solvent. Triturate the residue with water (10 ml) and collect the product by filtration. Wash with $EtO_2$ (3×20 ml) and dry the product in vacuo.

Add 6M HCl in dioxane (10 ml), stir 10 minutes, and evaporate the solvent. Purify on reverse phase HPLC (C−18 column; $H_2O$:$CH_3CN$:$CF_3COOH$, 549:449:2). Add 1N HCl (3 ml) and evaporate the solvent to obtain the title compound. FAB mass spec:(M+1)/e=699 (M-HCl).

Using the methods similar to those described in Example 1 but substituting appropriate starting materials in Steps A and B, the compounds listed in the following table were prepared. In the compounds listed, $R_1$ is —$CH_2CONH_2$, $R_2$ is 2-propyl, $X_1$-$X_3$ are —CONH—, $X_4$ is trans vinylene, and $X_5$ is ethylene:

| Example | $R_3$ | $R_4$ | $R_5$ | FAB Ms (M + 1) |
|---|---|---|---|---|
| 3 |  4-HOC₆H₄-CH₂- |  C₆H₅-CH₂CH₂CH₂- | 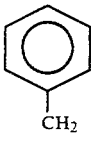 C₆H₅-CH₂- | 714 |
| 4 | 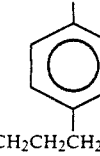 C₆H₅-CH₂- | 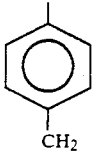 4-HO-C₆H₄-CH₂CH₂CH₂- | 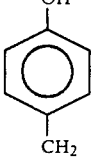 4-HO-C₆H₄-CH₂- | 730 |
| 5 | 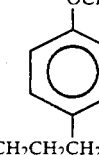 4-HO-C₆H₄-CH₂- |  4-CH₃O-C₆H₄-CH₂CH₂CH₂- |  4-CH₃O-C₆H₄-CH₂- | 774 |
| 6 | 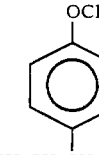 C₆H₅-CH₂- | 4-CH₃O-C₆H₄-CH₂CH₂CH₂- | 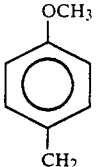 4-CH₃O-C₆H₄-CH₂- | 758 |

The compounds of this invention are useful in view of their pharmacological properties. In particular, compounds of this invention possess activity as antihypertensive agents, as evidenced by their ability to reduce blood pressure in mammals in which the blood pressure has become abnormally elevated.

The compounds of this invention can be combined with pharmaceutical carriers, to prepare conventional pharmaceutical compositions suitable for parenteral or oral administration. Such pharmaceutical compositions are useful in the treatment of cardiovascular disorders and particularly mammalian hypertension.

The effective daily antihypertensive dose ($ED_{50}$) of the compounds of this invention will typically be in the range of about 10 to about 100 mg/kg of mammalian weight, administered in single or divided doses. The exact dose to be administered is determined by the attending clinician and is dependent upon where the particular compounds lies within the above quoted range, as well as upon the age, weight and condition of the individual.

Generally, in treating humans having hypertension, the compounds of this invention may be administered to patients in need of such treatment in a dosage range of about 10 to about 500 mg per patient generally given several times a day, thus giving a total daily dose of from about 10 to about 2000 mg per day.

The compositions of the present invention can be administered orally or parenterally. Typical injectable formulations include solutions and suspensions. Typical oral formulations include tablets, capsules and elixirs. Also contemplated are mechanical delivery systems, e.g. transdermal dosage forms.

Following are typical examples of oral and parenteral formulation, wherein "active" refers to a compound of formula I.

EXAMPLE 7

| Capsule | Amount (mg) | |
| --- | --- | --- |
| Active Ingredient | 250.0 | 125.0 |
| Lactose | 173.0 | 86.5 |
| Corn Starch | 75.0 | 37.5 |
| Magnesium stearate | 2.0 | 1.0 |
| | 500.0 | 250.0 |

Blend the active ingredient, lactose, and corn starch until uniform; then blend the magnesium stearate into the resulting powder. Encapsulate the mxiture into suitably sized two-piece hard gelatin capsules.

EXAMPLE 8

| Tablet | Amount (mg) | |
| --- | --- | --- |
| Active Ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |
| | 500.0 | 250.0 |

Blend the active ingredient with the lactorse until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

EXAMPLE 9

| Injectable Solution | mg/ml |
| --- | --- |
| Active ingredient | 5.00 |

| Injectable Solution | mg/ml |
| --- | --- |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at 60°–70° C. and cool the solution to 25°–25° C. Charge and dissolve all other excipients and the active ingredient. Bring the solution to final volume, filter it through a sterlizing membrane and fill into sterile containers.

We claim:

1. A compound represented by the formula

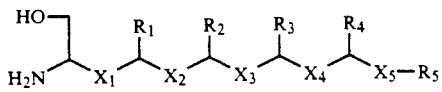

wherein $R_1$ is lower alkyl or $-CH_2CONR_6R_7$;

$R_2$, $R_3$, $R_4$ and $R_5$ are independently lower alkyl, cycloalkyl lower alkyl, aryl lower alkyl, heteroaryl lower alkyl, aryl lower alkoxy, substituted aryl lower alkyl, wherein the aryl portion is substituted with 1–3 substituents independently selected from lower alkyl, hydroxy, lower alkoxy and halogeno, substituted heteroaryl lower alkyl wherein the substituents on the heteroaryl portion are as defined for aryl lower alkyl, substituted cycloalkyl lower alkyl wherein the substituents on the cycloalkyl portion are as defined for aryl lower alkyl, and substituted aryl lower alkoxy wherein the substituents are as defined for aryl lower alkyl;

$R_6$ and $R_7$ are independently hydrogen or lower alkyl;

$X_1$, $X_2$, $X_3$, $X_4$ and $X_5$ are independently

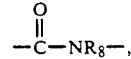

cis or trans $-CH_8=CR_9-$, $-CHR_8CHR_9-$, $-CN_2NR_8-$,

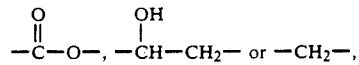

provided that when $R^4$ is methyl, $X_4$ is not $-CONH-$;

$R_8$ and $R_9$ are independently hydrogen or lower alkyl;

and the pharmaceutically acceptable salts thereof.

2. A compound of claim 1 wherein $R_1$ is methyl or $-CH_2CONH_2$.

3. A compound of claim 1 wherein $R_2$ is 2-propyl.

4. A compound of formula 1 wherein $R_3$, $R_4$ and $R_5$ are independently aryl lower alkyl or substituted aryl lower alkyl.

5. A compound of claim 1 wherein $R_3$ and $R_5$ are independently benzyl, 4-hdyroxybenzyl or 4-methoxybenzyl.

6. A compound of claim 1 wherein $R_4$ is phenylpropyl, 4-hydroxyphenylpropyl or 4-methoxyphenylpropyl.

7. A compound of claim 1 wherein $X_1$, $X_2$ and $X_3$ are each —CONH—.

8. A compound of claim 1 wherein $X_4$ is trans vinylene.

9. A compound of claim 1 wherein $X_5$ is ethylene.

10. A compound of claim 1 wherein Rl is methyl or —CH$_2$CONH$_2$; $R_2$ is 2-propyl; $X_1$, $X_2$ and $X_3$ are -CONH-; $X_4$ is trans vinylene; and $X_5$ is ethylene.

11. A compound of claim 10 wherein $R_3$, $R_4$ and $R_5$ are independently aryl lower alkyl or substituted aryl lower alkyl.

12. A compound of claim 11 wherein $R_3$ and $R_5$ are independently benzyl, 4-hydroxybenzyl or 4-methoxybenzyl and $R_4$ is phenylpropyl, 4-hydroxyphenylpropyl or 4-methoxyphenylpropyl.

13. Compounds of claim 12 wherein $R_3$ and $R_5$ are benzyl and $R_4$ is phenylpropyl;

$R_3$ is 4-hydroxybenzyl, $R_5$ is benzyl and $R_4$ is phenylpropyl;

$R_3$ is benzyl, $R_5$ is 4-hydroxybenzyl and $R_4$ is 4-hydroxyphenylpropyl;

$R_3$ is 4-hydroxybenzyl, $R_5$ is 4-methoxybenzyl and $R_5$ is 4-methoxyphenylpropyl; and $R_3$ is benzyl, $R_5$ is 4-methoxybenzyl, and $R_5$ is 4-methoxyphenylpropyl.

14. A method of treating hypertension in a mammal comprising administering to a hypertensive mammal an anti-hypertensive effective amount of a compound of claim 1.

15. An anti-hypertensive pharmaceutical composition comprising an anti-hypertensive effective amount of a compound of claim 1 in combination with a pharmaceutically acceptable carrier.

* * * * *

UNITED STATES PATENT AND TRADEMARK OFFICE
CERTIFICATE OF CORRECTION

PATENT NO. : 5,047,399

DATED : September 10, 1991

INVENTOR(S) : Laura S. Lehman, Michael F. Czarniecki

It is certified that error appears in the above-identified patent and that said Letters Patent is hereby corrected as shown below:

In column 1, line 54, delete "$-\underset{\underset{\text{O}}{|}}{\text{C}}-\text{CH}_2-$ or $-\underset{\underset{\text{O}}{\|}}{\text{C}}-\text{CH}_2-$"

and insert instead -- $-\underset{\underset{\text{OH}}{|}}{\text{C}}-\text{CH}_2-$ or $-\underset{\underset{\text{O}}{\|}}{\text{C}}-\text{CH}_2-$ --.

In column 10, line 50, delete "$-\text{CH}_2-$" and insert instead

-- $-\underset{\underset{\text{O}}{\|}}{\text{C}}-\text{CH}_2-$ --.

UNITED STATES PATENT AND TRADEMARK OFFICE
CERTIFICATE OF CORRECTION

PATENT NO. : 5,047,399

DATED : September 10, 1991

INVENTOR(S) : Laura S. Lehman, Michael F. Czarniecki

It is certified that error appears in the above-identified patent and that said Letters Patent is hereby corrected as shown below:

In column 11, line 6, delete "R1" and insert instead -- $R_1$ --.

Signed and Sealed this

Seventeenth Day of December, 1991

*Attest:*

HARRY F. MANBECK, JR.

*Attesting Officer*      *Commissioner of Patents and Trademarks*